US010376298B2

(12) United States Patent
Fischer et al.

(10) Patent No.: US 10,376,298 B2
(45) Date of Patent: Aug. 13, 2019

(54) MEDICAL CUTTING INSTRUMENT

(71) Applicant: Aesculap AG, Tuttlingen (DE)

(72) Inventors: Kay Fischer, Tuttlingen (DE); Michael Benk, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 326 days.

(21) Appl. No.: 15/356,835

(22) Filed: Nov. 21, 2016

(65) Prior Publication Data
US 2017/0151006 A1 Jun. 1, 2017

(30) Foreign Application Priority Data
Nov. 30, 2015 (DE) .......................... 10 2015 120 725

(51) Int. Cl.
*A61B 17/88* (2006.01)
*A61B 17/00* (2006.01)
(52) U.S. Cl.
CPC .... *A61B 17/8863* (2013.01); *A61B 17/00234* (2013.01); *A61B 2017/0046* (2013.01); *A61B 2017/00407* (2013.01); *A61B 2017/00424* (2013.01)
(58) Field of Classification Search
CPC .......... A61B 17/8863; A61B 17/00234; A61B 17/285; A61B 17/295; A61B 2017/00407; A61B 2017/00424; A61B 2017/0046; B25B 7/12; B26B 17/00; B26B 17/02
See application file for complete search history.

(56) References Cited

U.S. PATENT DOCUMENTS

| 1,592,017 | A | 7/1926 | Campen |
| 5,836,937 | A | 11/1998 | Holmes |
| 6,058,820 | A | 5/2000 | Rinner |
| 7,073,261 | B1 * | 7/2006 | Collins ..................... A01G 3/02 30/134 |
| 7,913,400 | B2 * | 3/2011 | Larkin .................... B26B 17/02 30/187 |
| 8,127,454 | B1 | 3/2012 | Gao |
| 8,784,420 | B2 * | 7/2014 | Steele ................ A61B 17/8863 606/79 |
| 2002/0069537 | A1 | 6/2002 | Wenzler |
| 2006/0122611 | A1 | 6/2006 | Morales et al. |

(Continued)

FOREIGN PATENT DOCUMENTS

| DE | 9000027 | 4/1990 |
| DE | 20018390 | 2/2001 |
| DE | 10326690 | 4/2005 |

(Continued)

*Primary Examiner* — Eric S Gibson
(74) *Attorney, Agent, or Firm* — Lipsitz & McAllister, LLC

(57) ABSTRACT

The invention relates to a medical instrument for severing connecting rods, in particular, of implanted spinal column stabilization systems, which comprises a first cutting element and a second cutting element which are pivotal relative to each other about a pivotal axis, a first handle element and a second handle element which are moveable relative to each other, and a force transmission device which is coupled to the first and the second handle element on the one hand and to the first and the second cutting element on the other for the purposes of transferring an actuating force from the first and second handle element to the first and second cutting element.

20 Claims, 8 Drawing Sheets

(56) References Cited

U.S. PATENT DOCUMENTS

2008/0249532 A1   10/2008   Schoutens et al.

FOREIGN PATENT DOCUMENTS

| DE | 202007007880 | 9/2007 |
| EP | 1138266 | 10/2001 |
| EP | 1201194 | 5/2002 |
| FR | 2929500 | 10/2009 |
| WO | 02/089659 | 11/2002 |

* cited by examiner

MEDICAL CUTTING INSTRUMENT

CROSS-REFERENCE TO RELATED APPLICATIONS

This application claims the benefit of German application number 10 2015 120 725.7 filed on Nov. 30, 2015, which is incorporated herein by reference in its entirety and for all purposes.

FIELD OF THE INVENTION

The present invention relates to medical instruments for severing connecting rods generally, and more specifically to a medical instrument for severing connecting rods, in particular, of implanted spinal column stabilization systems, comprising a first cutting element and a second cutting element which are pivotal relative to each other about a pivotal axis, a first handle element and a second handle element which are moveable relative to each, and a force transmission device which is coupled to the first and the second handle element on the one hand and to the first and the second cutting element on the other for the purposes of transferring an actuating force from the first and second handle element to the first and second cutting element.

BACKGROUND OF THE INVENTION

A medical instrument of the type described hereinabove is known from U.S. Pat. No. 5,836,937 for example. Connecting rods can be severed in the manner of a bolt cutter in a simple manner with such an instrument. Hereby, one problem in particular is the size of the instrument which, in practice, does not enable it to be employed in a minimally invasive procedure. In addition, an impulse which occurs during the process of severing the connecting rod cannot be accommodated in a secure manner.

Furthermore, instruments are known from U.S. Pat. No. 6,058,820 as well as U.S. Pat. No. 8,127,454 B1 in which the rod has to be pushed through the instrument. However, due to the size and construction thereof, instruments of this type are unable to sever a connecting rod that is already implanted and fixed to a spinal column.

Consequently, it would be desirable to provide a medical instrument with which, in particular, the process of severing connecting rods that are already implanted can be accomplished in a simple and safe manner.

SUMMARY OF THE INVENTION

In a first aspect of the invention a medical instrument for severing connecting rods, in particular, of implanted spinal column stabilization systems, comprises a first cutting element and a second cutting element which are pivotal relative to each other about a pivotal axis, a first handle element and a second handle element which are moveable relative to each other, and a force transmission device which is coupled to the first and the second handle element on the one hand and to the first and the second cutting element on the other for the purposes of transferring an actuating force from the first and second handle element to the first and second cutting element. The first handle element and the second handle element are arranged or formed such as to be rotatable relative to each other about a handle axis and/or such as to be displaceable or adapted to be screwed relative to each other parallel to the handle axis. The handle axis and the pivotal axis run transversely to each other.

BRIEF DESCRIPTION OF THE DRAWINGS

The foregoing summary and the following description may be better understood in conjunction with the drawing figures, of which.

DETAILED DESCRIPTION

Figure 1:
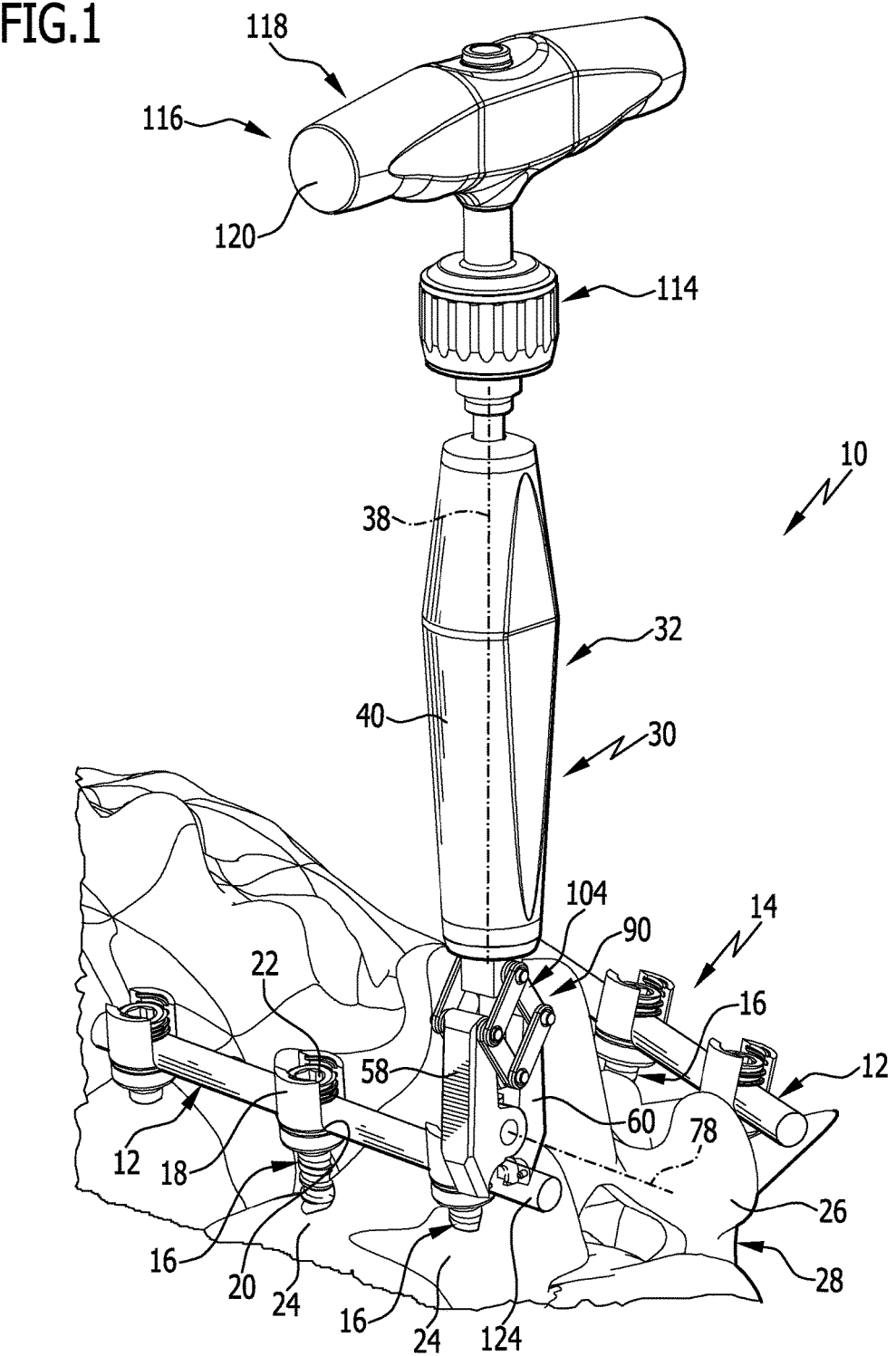
FIG. 1: shows a perspective overall view of the placement of a cutting instrument on a pre-implanted connecting rod for the purposes of cutting off a protruding end thereof.
Figure 2:
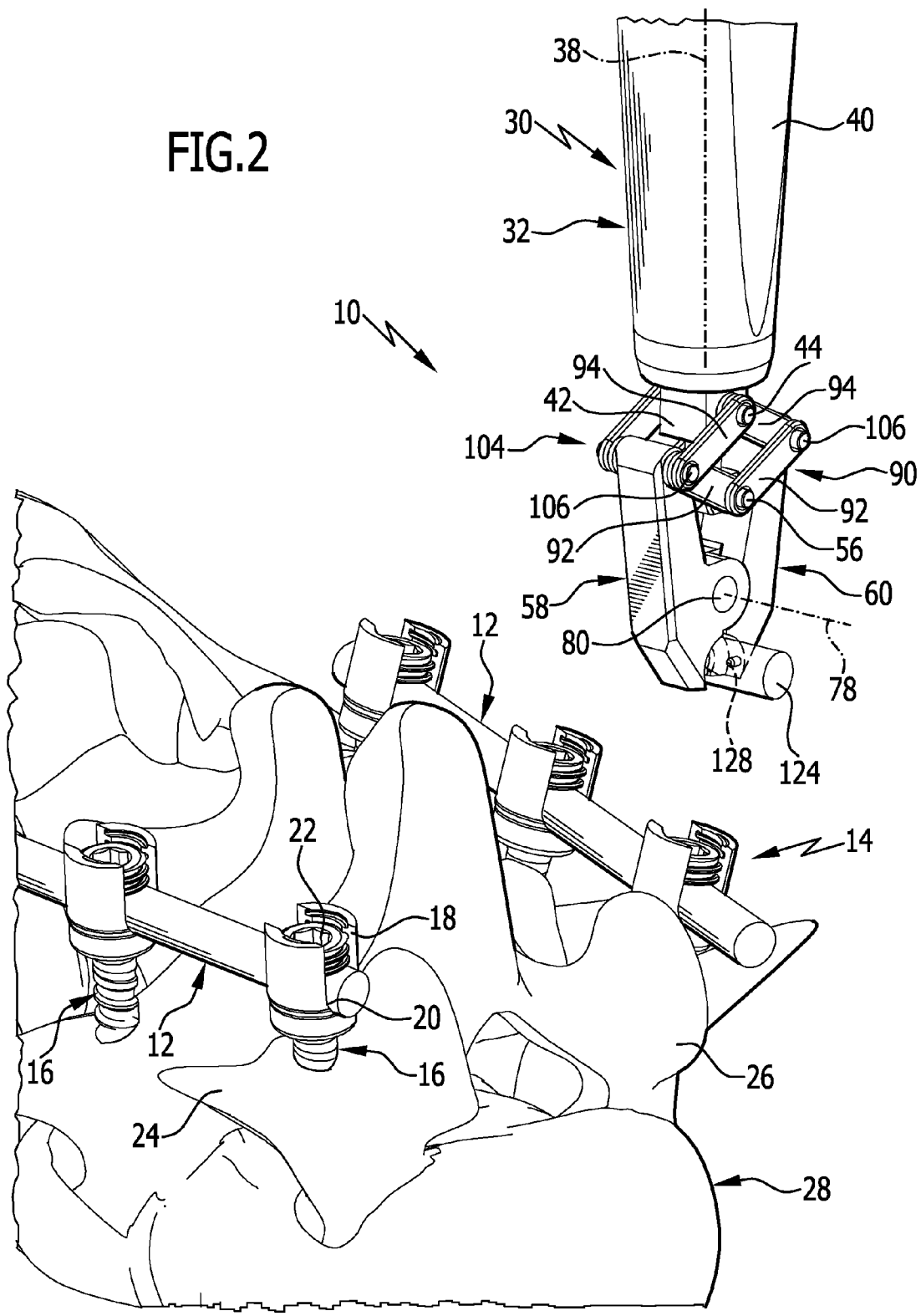
FIG. 2: a view similar to FIG. 1, but after the protruding end of the connecting rod has been cut off.
Figure 3:
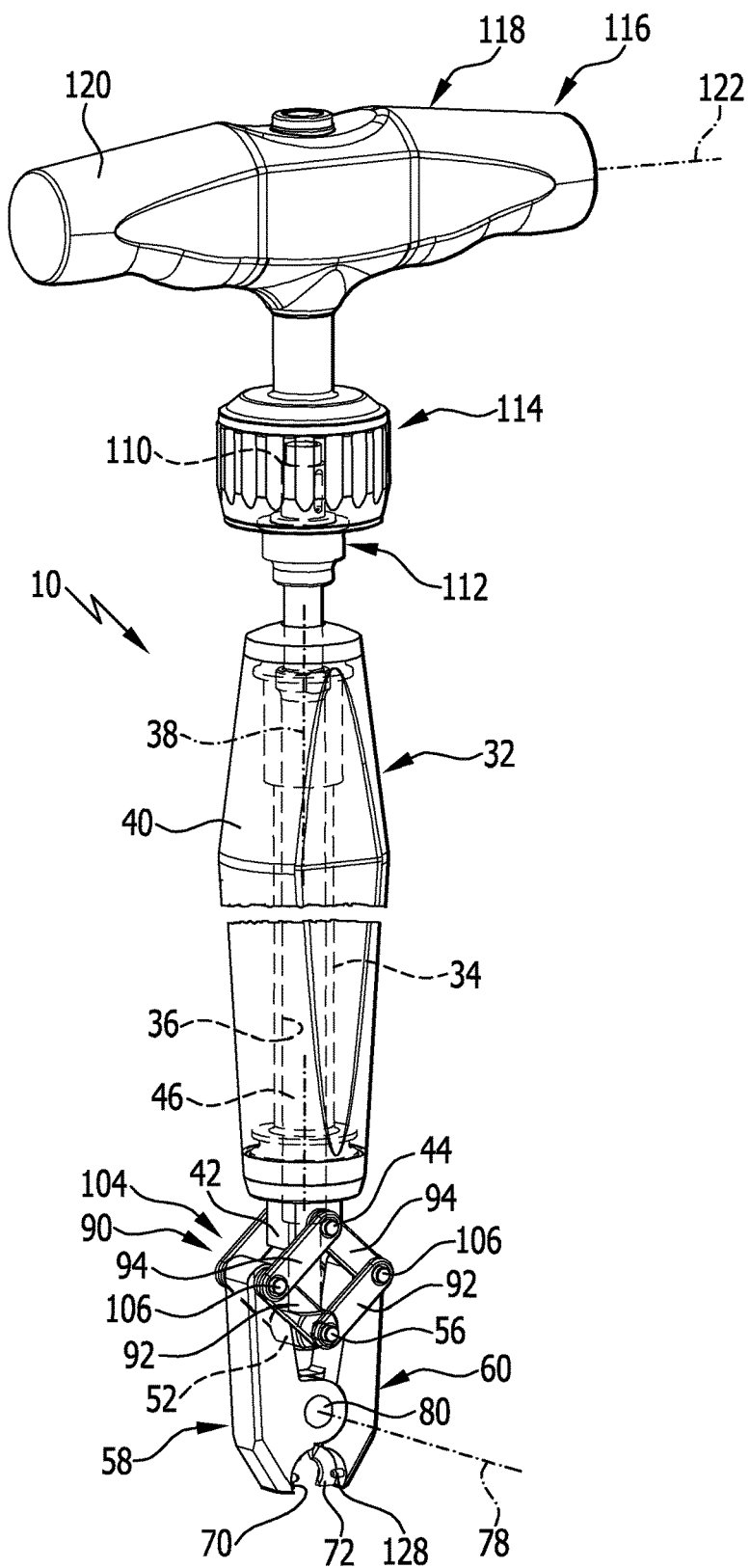
FIG. 3: a partly cutaway perspective view of the cutting instrument illustrated in FIG. 1.
Figure 4:
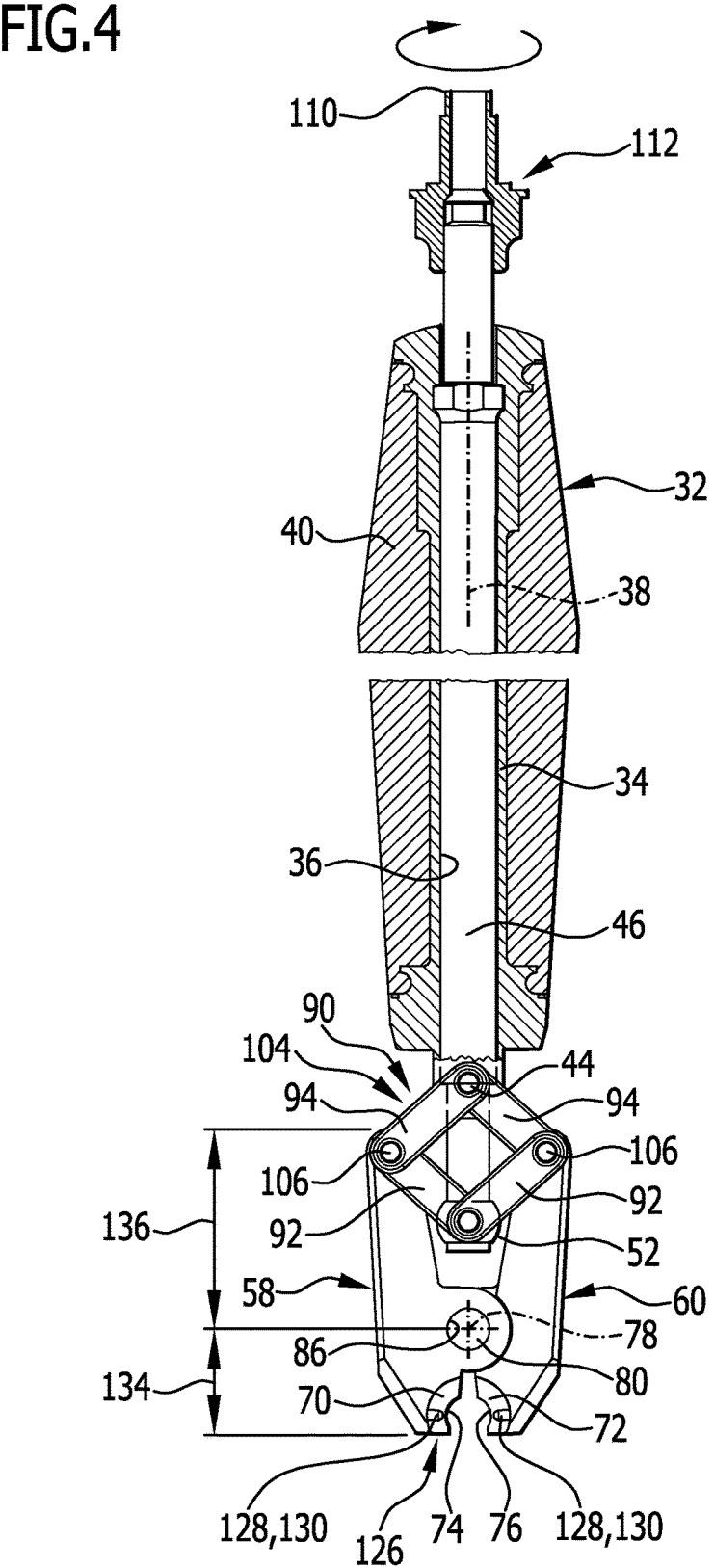
FIG. 4: a partly cutaway, partly sectional side view of the instrument depicted in FIG. 3.
Figure 5:
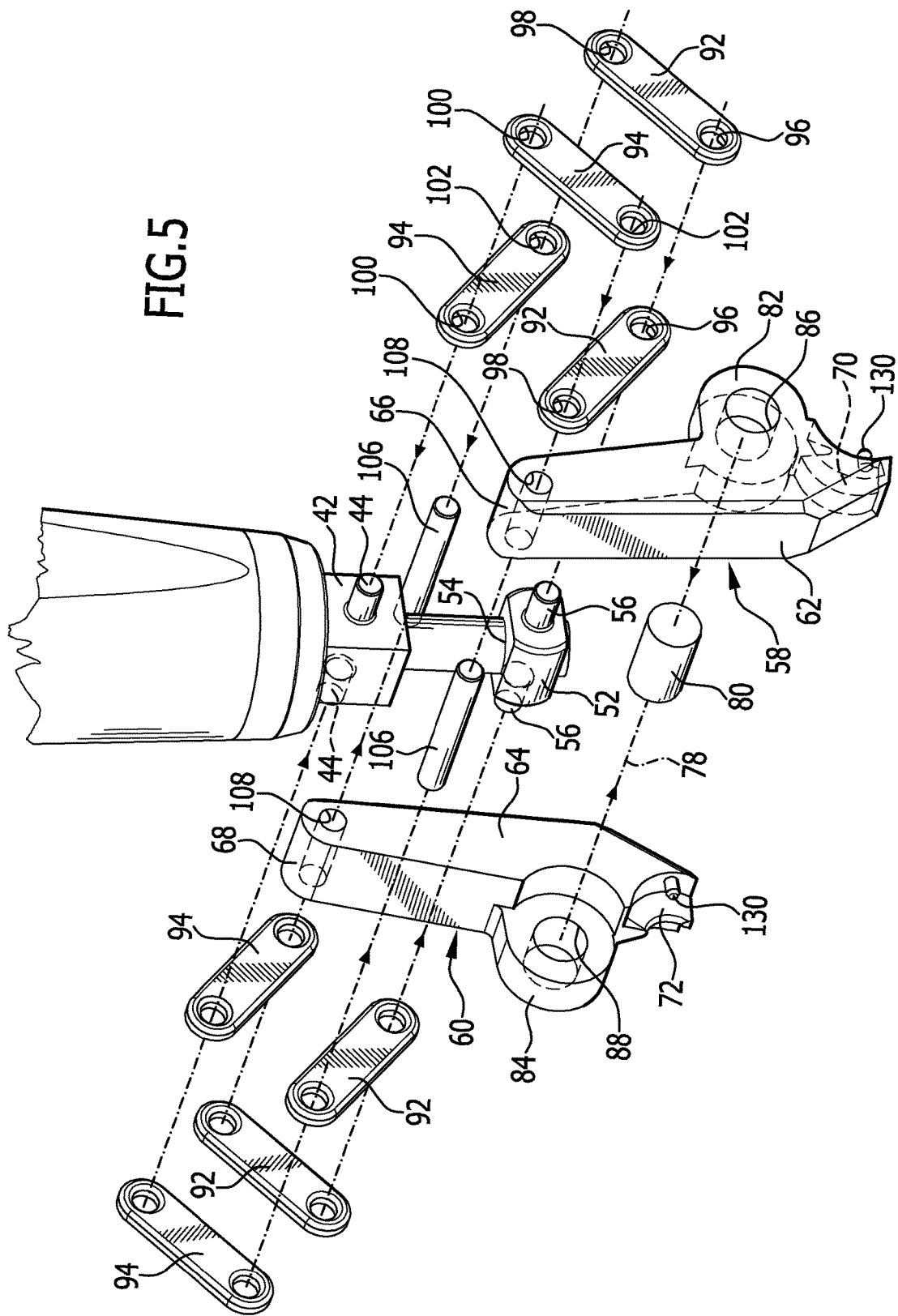
FIG. 5: an exploded illustration of a distal end of the cutting instrument depicted in FIG. 3.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical instrument for severing connecting rods, in particular, of implanted spinal column stabilization systems, comprising a first cutting element and a second cutting element which are pivotal relative to each other about a pivotal axis, a first handle element and a second handle element which are moveable relative to each other, and a force transmission device which is coupled to the first and the second handle element on the one hand and to the first and the second cutting element on the other for the purposes of transferring an actuating force from the first and second handle element to the first and second cutting element, wherein the first and the second handle element are arranged or formed such as to be rotatable relative to each other about a handle axis and/or such as to be displaceable or adapted to be screwed relative to each other parallel to the handle axis, and wherein the handle axis and the pivotal axis run transversely to each other.

The further development that is proposed makes it possible to produce a compact structure for the instrument in a simple manner. In particular, the handle axis and the pivotal axis can run perpendicularly to each other. In contrast to the instruments known from the state of the art in which the handle axis and the pivotal axis run in parallel with each other, the handle elements can then be twisted relative to each other about a longitudinal axis of one of the two handle elements for example or can be displaced or rotated relative thereto. This permits, in particular, an instrument to be constructed which is particularly slim and compact and hence one which can also be employed where there is only a restricted amount of space, especially in the case of minimally invasive surgical procedures. It is thus possible in particular to cut off the protruding ends of a connecting rod or to sever a connecting rod that is fixed to two or more implants that are in the form of bone screws for example in a region between the two implants. This process of cutting off and severing connecting rods is possible both in the body of a patient and externally thereof.

It is advantageous if the first handle element is in the form of a sleeve and if the force transmission device comprises a shaft which is coupled to the second handle element and is mounted such as to be displaceable, adapted to be screwed and/or to be rotatable in the sleeve. Such an arrangement makes it possible in particular for a surgeon to hold the medical instrument firmly by the first handle element and to displace, screw and/or rotate the shaft in the sleeve with the aid of the second handle element. For this purpose, the second handle element in particular can be coupled directly or indirectly to the shaft.

In order to produce a rotation of the shaft relative to the sleeve in a simple manner, it is advantageous if the instrument comprises a ratchet mechanism which couples the second handle element to the shaft. For example, the second handle element could also be a part of the ratchet mechanism if this is in the form of a ratchet handle. Thus in particular, without releasing the second handle element, a surgeon can then cause the shaft to gradually rotate relative to the sleeve by alternately rotating the second handle element relative to the first handle element about the handle axis in an anticlockwise direction and then again in the clockwise direction.

Preferably, the second handle element and the shaft are connected to each other such as to be immovable relative to one another. In particular, they can be formed in one piece or be connected to one another by force-locking engagement and/or a substance-to-substance bond and/or positive engagement. Such an arrangement is especially advantageous in the case where the shaft is arranged or formed to be displaceable and in particular, to be exclusively displaceable relative to the sleeve parallel to the handle axis.

The instrument can be handled more ergonomically in a simple manner if the second handle element defines a longitudinal axis which runs transverse to the handle axis. In particular, a T-shaped instrument handle which a surgeon can easily grip and move can then be formed in a simple manner.

In accordance with an embodiment, provision may be made for the second handle element and the ratchet mechanism to form a T-shaped or substantially T-shaped ratchet handle. Optionally, such a ratchet handle can be connectible to the shaft in releasable manner in order to remove the ratchet handle especially for cleaning purposes.

The instrument can be constructed in a particularly compact manner if the first and the second cutting element are mounted directly on one another in pivotal manner. In particular, this enables a distal end of the instrument to be formed such as to define a minimum cross section so that it can be introduced in a simple manner through a point of access into the interior of the body of a patient even in the course of a minimally invasive surgical procedure in order to sever a connecting element that is already fixed to the spinal column.

Furthermore, it can be advantageous if the medical instrument comprises a rotationally symmetrical or substantially rotationally symmetrical bearing pin for coupling the first and the second cutting element, which bearing pin defines the pivotal axis. The bearing pin makes it possible, in particular, to couple the first and the second cutting element directly together as the bearing pin is held on both the first and the second cutting element.

It is expedient if the bearing pin is held on the first cutting element on a first bearing projection, if the second cutting element comprises a bearing pin seating and if the bearing pin is held in the bearing pin seating such as to be rotatable. In particular, the bearing pin can be held on the first cutting element such as to be immovable. A stable articulated coupling between the first cutting element and the second cutting element can thereby be formed in a simple manner.

The coupling between the two cutting elements can be realized in a simple manner if the bearing pin seating is in the form of a boring. In particular, the boring can be formed in a second bearing projection which is formed on the second cutting element. In particular, the second bearing projection can be arranged or formed such that it is oriented in the direction of the first cutting element.

It is expedient if the first cutting element comprises a bearing pin seating in which the bearing pin is held moveably or immovably. In particular, the bearing pin seating can be in the form of a boring. In this way, a pivotal bearing for the articulated coupling of the first and the second cutting element can be realized in a simple manner.

In accordance with an embodiment, provision may be made for the first cutting element to comprise a distal end having a first cutter and a proximal first coupling end, for the second cutting element to comprise a distal end having a second cutter and a proximal second coupling end, for the first coupling end and the second coupling end to be coupled to the force transmission device and for the pivotal axis to run between the distal ends and the first and the second coupling end. In particular, the arrangement described makes it possible to move the first and the second cutter relative to each other, in particular, towards one another for the purposes of severing a connecting element, namely, in that the first coupling end and the second coupling end are moved towards one another or away from each other so that the two cutting elements are pivoted relative to each other about the pivotal axis.

In order to enable as large a cutting force as possible to be transmitted, it is advantageous if a spacing between the pivotal axis and the first and the second cutter is smaller than a spacing between the pivotal axis and the first and the second coupling end. Taking into consideration the lever principle, reinforcement of the actuating force can then be given by the ratio of the distances between the pivotal axis and the cutters on the one hand and the pivotal axis and the coupling ends on the other.

It is expedient if the force transmission device comprises at least two first coupling members and at least two second coupling members, if the at least two first coupling members couple the first coupling end and the second coupling end to a distal end of the shaft in articulated manner and if the at least two second coupling members couple the first and the second coupling ends to the first handle element in articulated manner. In particular, the at least two second coupling members can be coupled to a distal end of the first handle element in articulated manner. Coupling the at least two first and at least two second coupling members to the shaft and to the first handle element in articulated manner in the manner described, makes it possible in particular to transform an axial movement of the shaft and the first handle element relative to each other into a pivotal movement of the first and the second cutting elements relative to each other. In other words, a force or a torque can be introduced parallel to the handle axis which is then transformed by the force transmission device into a torque about the pivotal axis.

A particularly stable arrangement of the instrument can be achieved if four first and four second coupling members are provided.

A particularly simple and stable transmission of force to the two cutting elements as a result of a relative movement of the shaft and the first handle element can be achieved in particular in that the at least two first coupling members and the at least two second coupling members form a scissor joint.

It is advantageous if a distal end of the shaft carries a coupling element which is held on a distal end of the shaft in rotatable manner and/or such that it is adapted to be screwed. In this way, a relative movement of the distal end of the shaft and the coupling element can take place without the coupling element itself rotating about the handle axis. For example, the coupling element can be provided with an internal thread which corresponds to an external thread formed at the distal end of the shaft so that a screwing movement of the shaft causes a movement of the coupling element parallel to the handle axis without the coupling element rotating about the handle axis.

Preferably, the coupling element is arranged to be displaceable relative to the first handle element parallel to the handle axis. In this way, the coupling element can be moved away from a distal end of the first handle element or back towards it whereby, in cooperation with the coupling members, the cutting elements can be moved away from each other or towards one another. In particular, it can thereby be arranged that a rotation of the coupling element relative to the first handle element is prevented. Hence, in particular, a simple coupling of the shaft and the first handle element on the one hand can be produced by a scissor member with the two cutting elements.

For cleaning purposes in particular, it is expedient if the first handle element and the second handle element are connectible to one another in releasable manner.

In accordance with an embodiment, provision may be made for the first and/or the second cutting element to comprise at least one holding member for holding a severed piece of connecting rod after the process of severing a connecting rod. The at least one holding member on the first and/or second cutting element can, in particular, be part of a retaining device which may be provided in order to prevent a severed piece of connecting rod from flying about in an uncontrolled manner or a distal end of the instrument from wobbling about in the operation area in an uncontrolled manner as a result of a cutting impulse which is produced when severing the connecting rod, which is something that could lead to serious injuries. In particular, it can be taken into consideration during the process of positioning and arranging the at least one holding member that a connecting rod will typically shear off when the diminuation of a cross section is approximately 50%.

The retaining device can be formed in a simple manner if the at least one holding member is in the form of a holding projection which projects in the direction of the respective other cutting element. In particular, the holding projection can be arranged in such a manner that, during the process of severing a connecting rod, it protrudes to the level of a maximum diameter of the connecting rod which has a circular cross section for example so that such a connecting rod can also be held securely by the retaining device.

The instrument can be formed in a particularly compact manner if the at least one holding member is arranged or formed such as to be adjacent to one of the two cutters. In particular, a severed piece of connecting rod can then be gripped and held in a simple and secure manner.

Preferably, a free end of the least one holding member is set back with respect to a boundary surface which is defined by a cutting edge of the respective cutting element. In this way, the connecting rod can firstly be grasped by the cutting edges of the cutting elements and partly cut through before the at least one holding member can touch and seize the piece of connecting rod.

It is expedient if the at least one holding member is made of a material other than the material from which the first and/or the second cutting element is formed. For example, the two cutting elements and in particular the cutting edges or cutters thereof can be made of a hard steel, the at least one holding member made of a somewhat softer metal or of a plastics material in order to exhibit a certain amount of elasticity which will permit of a temporary deformation for example, namely, in the case in particular where the connecting rod is not yet completely severed but the at least one holding member is already resting on it.

In order to grip the connecting rod securely especially before it is severed and to prevent it from slipping insofar as possible, it is expedient for the first and/or the second cutting element to comprise a respective cutting edge which is directed substantially towards the other cutting element and which, in particular, is concavely curved away from the respective cutting element. In particular, the curvature of the cutting edge can be matched to an outer cross section of the connecting rod that is to be severed. Preferably, a radius defined by the cutting edges is somewhat smaller than a radius of the connecting rod that is to be severed.

A medical instrument 10 for severing connecting rods 12 of a spinal column stabilization system 14 is illustrated exemplarily in FIGS. 1 to 8.

The spinal column stabilization system 14 typically comprises a plurality of bone screws 16 which can, in particular, be in the form of polyaxial screws having forked screw heads 18, in the U-shaped seatings 20 whereof a connecting rod 12 can be fixed by means of a respective fixing screw 22.

Hereby, the bone screws 16 are usually screwed into pedicles 24 of the vertebrae 26 of a spinal column 28.

The instrument 10 is in the form of a rod cutter 30 and comprises a first handle element 32 which comprises a rotationally symmetrical sleeve 34 which defines a central channel 36 as well as a handle axis 38. For improved ergonomics, the sleeve 34 is surrounded by a handle shaft 40.

A distal end of the sleeve 34 protrudes from the handle shaft 40 and forms a substantially parallelepipedal connecting projection 42. Two bearing journals 44 protrude from this connecting projection in diametrically opposite directions.

A shaft 46, which is provided with an externally threaded section 50 extending from the distal end 48 thereof and which passes through the channel 36, is mounted in the first handle element 32 in rotatable manner.

A through-boring 54 which is provided with an internal thread and extends coaxially with respect to the handle axis 38 is formed in a substantially parallelepipedal coupling element 52 so that the coupling element 52 can be screwed onto the externally threaded section 50 in like manner to a nut on a bolt.

Two bearing journals 56 projecting in diametrically opposite directions project away from the coupling element 52 in like manner to those from the connecting projection 42. The bearing journals 44 and the bearing journals 56 are orientated in parallel with each other.

Furthermore, the instrument 10 comprises a first cutting element 58 as well as a second cutting element 60. These each comprise a respective base body 62 and 64. The first cutting element 58 has a first coupling end 66 and the second cutting element 60 a second coupling end 68. The coupling ends 66 and 68 are oriented substantially in the proximal direction.

Cutters 70 and 72 having sharpened cutting edges 74 and 76 are formed on the cutting elements 58 and 60 at the distal end thereof, said cutting edges substantially facing one another and being concavely curved in the direction oriented away from the respective cutting element 58 and cutting element 60.

The cutting elements 58 and 60 are mounted directly upon one another such as to be pivotal about a pivotal axis 78 which is defined by a cylindrical bearing pin 80. The spacing 134 of the cutters 70 and 71 from the pivotal axis 78 is smaller than the spacing 136 of the coupling ends 66 and 68 from the pivotal axis.

The first cutting element 58 comprises a first bearing projection 82 which is oriented substantially in the direction of the second cutting element 60, the second cutting element 60 comprises a second bearing projection 84 which is oriented substantially towards the first cutting element 58. The bearing projections 82 and 84 are provided with a respective boring 86 and 88 into which the bearing pin 80 is inserted. In particular, the bearing pin 80 can be fixed to one of the two bearing projections 82 or 84 by adhesion, soldering or welding for example. The bearing pin 80 can also be mounted such as to be rotatable in the two borings 86 and 88. In this case, it is preferable in a manner similar to a rivet, for a thickened portion of the pin to project somewhat from the borings 86 and 88 so that it is fixed such that it is not displaceable or is substantially not displaceable in the axial direction.

Furthermore, the instrument 10 comprises a force transmission device 90 for transferring an actuating force to the cutting elements. In the exemplary embodiment of the instrument 10 that is illustrated in the Figures, the force transmission device 90 comprises four identical first coupling members 92 and four identical second coupling members 94.

The first and second coupling members 92 and 94 are identical and are in the form of flat parallelepipedal joint platelets, wherein the first coupling members 92 comprise first openings 96 and second openings 98 which are each in the form of borings and are formed at the adjacent free ends of the coupling members 92. In analogous manner, the second coupling members 94 respectively comprise a third opening 100 and a fourth opening 102.

Together, the coupling members 92 and 94 form a scissor joint 104 which is coupled to the cutting elements 58 and 60 on the one hand and to the shaft 46 on the other by the coupling element 52 and the connecting projection 42 of the first handle element 32. The first openings 96 of the first coupling members 92 are held on the bearing journals 56 in pivotal manner, the third openings 100 of the second coupling members 94 being held on the bearing journals 44. The first and second coupling members 92 and 94 are connected together in articulated manner by two connecting pins 106. The connecting pins 106 extend through a respective second opening 98 as well as a fourth opening 102. Furthermore, the connecting pins 106 extend through borings 108 through the coupling ends 66 and 68 so that a short section of the connecting pins 106 projects out on both sides of the borings 10, which short sections serve for mounting the first and second coupling members 92 and 94.

In particular, the scissor members 104 ensure that the coupling element 52 remains at a defined aligned orientation relative to the connecting projection 42, namely, in such a manner that the bearing journals 44 and 56 remain aligned in parallel with one another. The connecting pins 106, the openings 96, 98, 100 and 102 and also the borings 108 are also aligned in parallel therewith.

If the shaft 46 is rotated in the sleeve 34 about the handle axis 38, then the end 48 of the shaft 46 is screwed into the coupling element 52 when twisted in a clockwise direction so that it is pulled in the direction of the connecting projection 42. This has the consequence that the coupling ends 66 and 68 are pivoted away from each other so that the cutters 70 and 72 move towards one another.

If one rotates the shaft 46 in the sleeve 34 in the counter-clockwise direction, then the end 48 of the shaft 46 unscrews from the coupling element 52. The coupling ends 66 and 68 move towards one another again so that the cutters 70 and 72 are parted from each other.

A proximal end 110 of the shaft 46 sticks out from the first handle element 32 at the proximal side. It is equipped with a coupling device 112 in the form of a ratchet mechanism which engages with an overall T-shaped ratchet handle 116 in order to form a ratchet 114. The ratchet handle 116 comprises a second handle element 118 having an ergonomically designed handle 120 which defines a longitudinal axis 122 that runs transverse to the handle axis 38. The handle 120 is symmetrical with reference to the handle axis 38. As described, the ratchet handle 116 is couplable to the shaft 46 in the manner of a releasable connection.

The protruding end sections 124 of connecting rods 12 can be cut off or the connecting rods 12 simply severed with the aid of the rod cutter 30.

Furthermore, the instrument 10 also comprises a retaining device 126 in order to prevent uncontrolled jettisoning of the end sections 124 after the severing process. This retaining device comprises two holding members 128 which are in the form of peg-like holding projections 130 that are substantially directed towards one another.

The holding projections 130 are arranged on the cutting elements 58 and 60 adjacent to the cutters 70 and 72 and cooperate with each other for the purposes of holding the cut-off end sections 124. The free ends 132 of the holding members 128 are set back somewhat with respect to the cutting edges 74 and 76 or with respect to the hollow cylindrical bounding surfaces defined thereby so that the cutting edges 74 and 76 first touch the rod when being brought into contact with a connecting rod 12, the ends 132 however only touching the connecting rod 12 when the cutting edges 74 and 76 have already penetrated somewhat into the connecting rod 12 and it has been partially cut.

The functioning of the instrument 10 is briefly described hereinafter.

First of all, the rod cutter 30 is made ready for placement on a connecting rod 12 by separating the cutters 70 and 72 from each other and by rotating the second handle element 118 relative to the first handle element 32.

Figure 6:
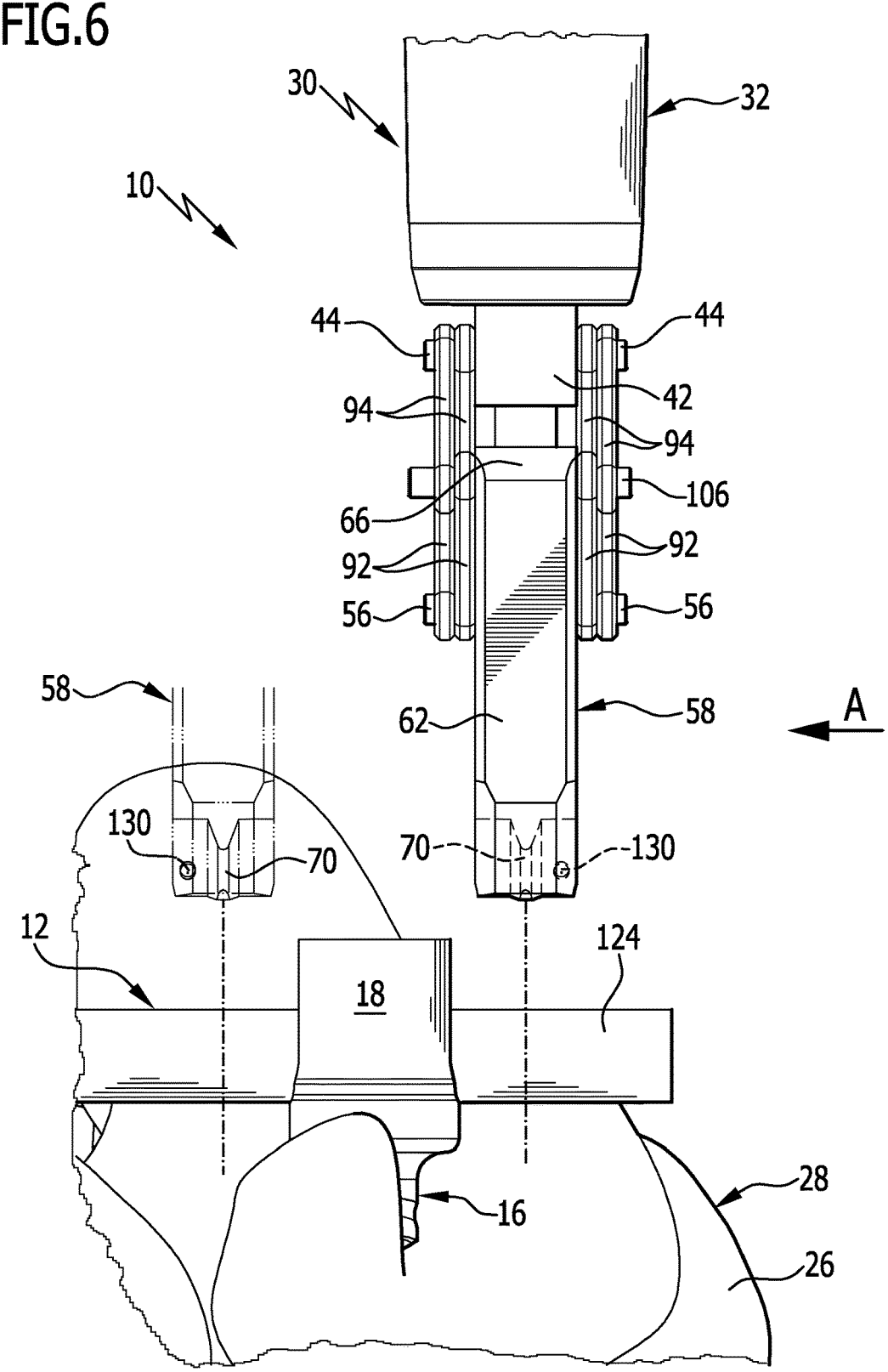
FIG. 6: a side view of the cutting instrument depicted in FIG. 3 before it is placed on a connecting rod that is to be severed.
Figure 7:
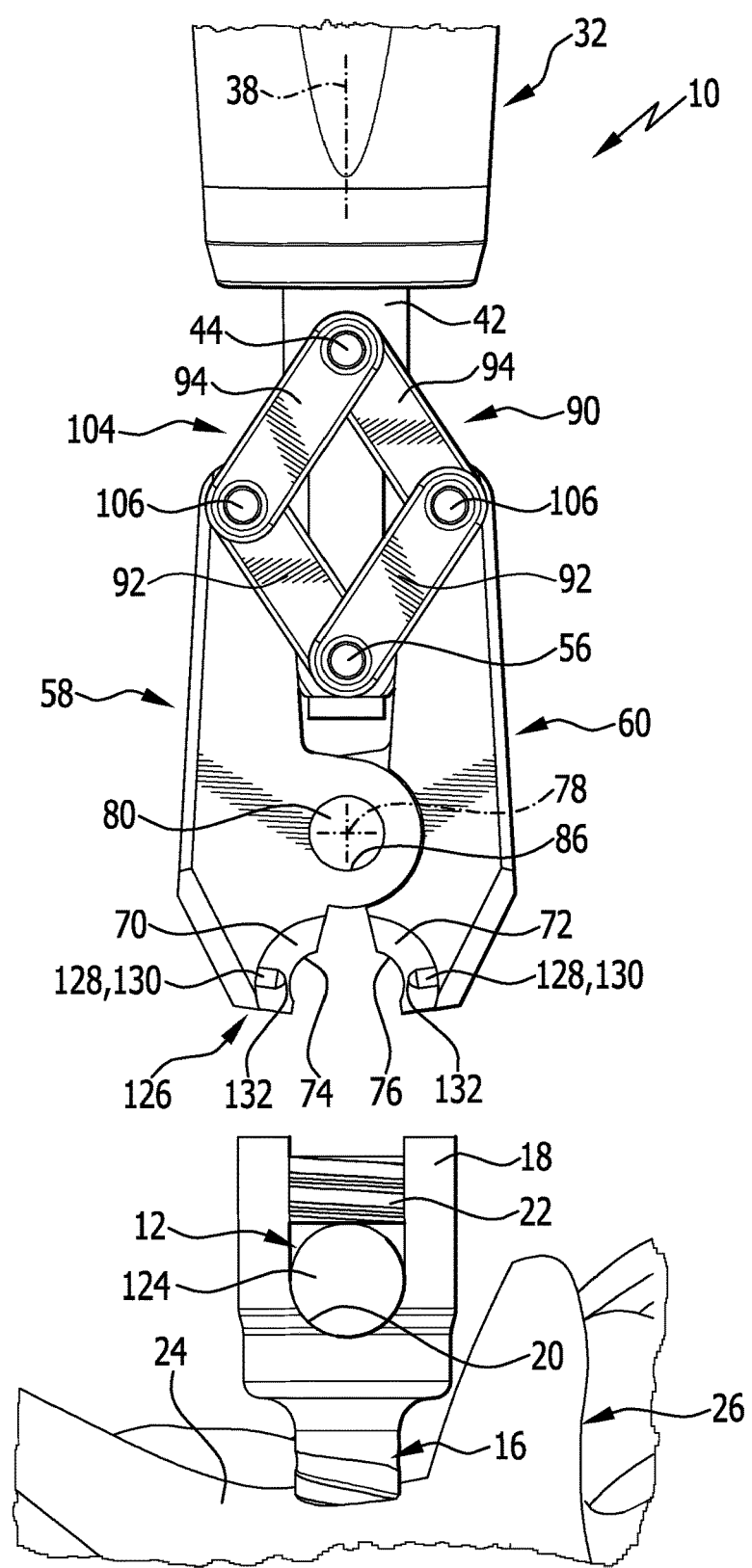
FIG. 7: a view of the arrangement depicted in FIG. 6 in the direction of the arrow A.

In an opened position of this type such as is illustrated in FIG. 7 for example, the rod cutter 30 can be placed on the connecting rod 12 from above as is schematically illustrated in FIG. 6 as well as in FIG. 1.

For the purposes of severing the connecting rod 12, the second handle element 118 is rotated relative to the first handle element 32 in the opposite direction so that the coupling element 52 is moved in the direction of the connecting projection 42. The cutters 70 and 72 are thereby pivoted about the pivotal axis 78 and the cutting edges 74 and 76 dig into the connecting rod 12.

Too deep an insertion of the rod cutter 30 into the body of the patient is not possible since the special shape of the cutting edges 74 and 76 forms a depth-limiting stop for the instrument 10.

Figure 8:
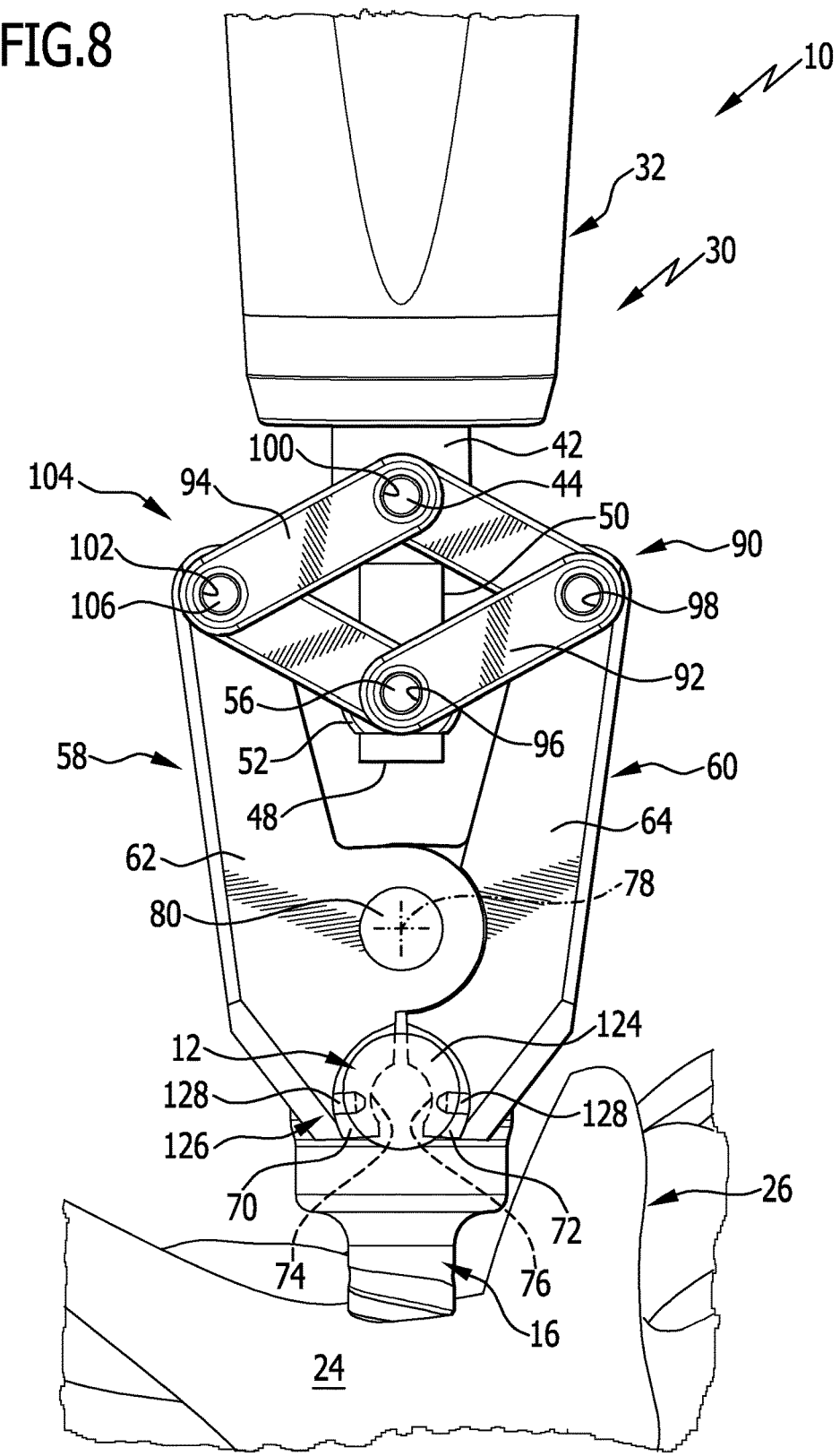
FIG. 8: a view similar to FIG. 7, but when severing the connecting rod.

As is illustrated schematically in FIG. 8, the ends 132 of the holding projections 130 rest on the end section 124 that is to be cut off or which has been cut off when the connecting rod 12 has been severed by the rod cutter 30 and they clamp the end section therebetween.

Optionally, the cutting elements 58 and 60 can be formed and mounted on one another in such a manner that the cutting edges 74 and 76 do not entirely fit together. This is possible, in particular, because the connecting rod will already have sheared off when the diminuation of a cross section thereof is approximately 50%.

The holding members 128 can be optionally replaceable. For example, the holding projections 130 can form the free ends of pins that are inserted into borings of the cutting elements 58 and 60.

The shape and length of the holding members 128 are adapted to the diminuation of the cross section that is necessary for severing the connecting rods 12 so that the connecting rod 12 will be held securely after the cutting or severing process, although a large amount of force for pressing the ends 132 into the connecting rods 12 does not have to be exerted.

The impulse that develops during the process of severing the connecting rods 12 is reduced by means of the special construction of the instrument 10 since a significantly more proportioned exertion of force is possible due to the rotary movement of the handle elements 32 and 118 relative to each other about the handle axis than in the case of a bolt cutter for example. A surgeon can promptly sense yielding of the connecting rod when he is closing the cutting elements 58 and 60 and can thereby adapt the force that needs to be applied for the severing process.

The cutters 70 and 72 are preferably formed from a material that is of sufficient hardness to sever the connecting rods 12 and they are usually made of titanium or CoCr alloys.

What is claimed is:

1. A medical instrument for severing connecting rods, in particular, of implanted spinal column stabilization systems, comprising:
    a first cutting element and a second cutting element which are pivotal relative to each other about a pivotal axis,
    a first handle element and a second handle element which are moveable relative to each other, and
    a force transmission device which is coupled to the first handle element and the second handle element and to the first cutting element and the second cutting element for the purpose of transferring an actuating force from the first handle element and the second handle element to the first cutting element and the second cutting element,
    wherein:
    the first handle element and the second handle element are arranged or formed at least one of to be rotatable relative to each other about a handle axis and to be movable relative to each other about the handle axis,
    the handle axis and the pivotal axis run transversely to each other,
    the first cutting element comprises a distal end having a first cutter with a first cutting edge,
    the second cutting element comprises a distal end having a second cutter with a second cutting edge,
    the first cutting edge is directed substantially towards the second cutting edge,
    the second cutting edge is directed substantially towards the first cutting edge, and
    the first cutter and the second cutter are pivotal with their respective cutting edges about the pivotal axis towards each other and away from each other in a plane running perpendicular to the pivotal axis so as to allow the medical instrument to be placed across a circumference of a connecting rod from above, with the pivotal axis parallel to a longitudinal axis of the connecting rod.

2. The medical instrument in accordance with claim 1, wherein the first handle element is in the form of a sleeve, further comprising a shaft which is coupled to the second handle element and is mounted at least one of:
    a) to be displaceable,
    b) adapted to be screwed, and
    c) rotatable in the sleeve.

3. The medical instrument in accordance with claim 2, further comprising a ratchet mechanism which couples the second handle element to the shaft.

4. The medical instrument in accordance with claim 3, wherein the second handle element and the ratchet mechanism form a T-shaped or a substantially T-shaped ratchet handle.

5. The medical instrument in accordance with claim 2, wherein the second handle element and the shaft are connected to one another such as to be immovable relative to each other.

6. The medical instrument in accordance with claim 2, wherein the distal end of the shaft carries a coupling element which at least one of:
    a) is held on the distal end of the shaft in a rotatable manner, and
    b) is adapted to be screwed onto the distal end of the shaft.

7. The medical instrument in accordance with claim 6, wherein the coupling element is arranged to be displaceable relative to the first handle element along the handle axis.

8. The medical instrument in accordance with claim 1, wherein the second handle element defines a longitudinal axis which runs transverse to the handle axis.

9. The medical instrument in accordance with claim 1, wherein the first cutting element and the second cutting element are mounted directly on one another in a pivotal manner.

10. The medical instrument in accordance with claim 1, further comprising a rotationally symmetrical or substantially rotationally symmetrical bearing pin for coupling the first cutting element and the second cutting element, which bearing pin defines the pivotal axis.

11. The medical instrument in accordance with claim 10, wherein the bearing pin is held one of:
    a) immovably on the first cutting element on a first bearing projection, wherein the second cutting element comprises a bearing pin seating, and the bearing pin is held in the bearing pin seating so as to be rotatable, and
    b) on the first cutting element on a first bearing projection, wherein the second cutting element comprises a bearing pin seating and the bearing pin is held in the bearing pin seating so as to be rotatable.

12. The medical instrument in accordance with claim 1, wherein:
    the first cutting element comprises a proximal first coupling end,
    the second cutting element comprises a proximal second coupling end, the first coupling end and the second coupling end are coupled to the force transmission device, and the pivotal axis runs between the distal ends and the first coupling end and the second coupling end.

13. The medical instrument in accordance with claim 12, wherein a spacing between the pivotal axis and the first cutter and the second cutter is smaller than a spacing between the pivotal axis and the first coupling end and the second coupling end.

14. The medical instrument in accordance with claim 12, wherein:

the force transmission device comprises at least two first coupling members and at least two second coupling members, the at least two first coupling members couple the first coupling end and the second coupling end to a distal end of the shaft in articulated manner, and the at least two second coupling members couple the first coupling end and the second coupling end to the first handle element in articulated manner.

15. The medical instrument in accordance with claim 14, wherein at least one of:

the medical instrument comprising four first and four second coupling members, and the at least two first coupling members and the at least two second coupling members form a scissor joint.

16. The medical instrument in accordance with claim 1, wherein at least one of the first cutting element and the second cutting element comprises at least one holding member for holding a severed piece of the connecting rod after the process of severing the connecting rod.

17. The medical instrument in accordance with claim 16, wherein the at least one holding member at least one of:

a) is in the form of a holding projection which projects in a direction of the respective other cutting element;

b) is arranged or formed such as to be adjacent to a cutting edge of one of the first cutting element and the second cutting element;

c) is made of a material other than the material from which at least one of the first cutting element and the second cutting element is formed.

18. The medical instrument in accordance with claim 16, wherein a free end of the at least one holding member is set back with respect to a boundary surface which is defined by a cutting edge of the respective cutting element.

19. The medical instrument in accordance with claim 1, wherein:

the first cutting edge is concavely curved away from the first cutting element, and the second cutting edge is concavely curved away from the second cutting element.

20. The medical instrument in accordance with claim 19, wherein one of:

a) a curvature of the first cutting edge and a curvature of the second cutting edge is matched to an outer cross section of the connecting rod that is to be severed and the curvature of the second cutting edge is matched to an outer cross section of the connecting rod that is to be severed; and b) a radius defined by the first cutting edge and the second cutting edge is smaller than a radius of the connecting rod that is to be severed.

* * * * *